(12) United States Patent
Wang et al.

(10) Patent No.: US 12,311,002 B2
(45) Date of Patent: *May 27, 2025

(54) **EXTRACT OF *GINKGO BILOBA* LEAVES AND PREPARATION METHOD THEREFOR**

(71) Applicant: SPH XING LING SCI. & TECH. PHARMACEUTICAL CO., LTD., Shanghai (CN)

(72) Inventors: Jun Wang, Shanghai (CN); Qi Gao, Shanghai (CN); Qin Shen, Shanghai (CN); Baozhong Zhu, Shanghai (CN); Dandan Wang, Shanghai (CN); Jinfeng Wang, Shanghai (CN); Yafang Wei, Shanghai (CN); Guoqin Zhu, Shanghai (CN)

(73) Assignee: SPH Xing Ling Sci. & Tech. Pharmaceutical Co., Ltd., Shanghai (CN)

( * ) Notice: Subject to any disclaimer, the term of this patent is extended or adjusted under 35 U.S.C. 154(b) by 1030 days.

This patent is subject to a terminal disclaimer.

(21) Appl. No.: 17/264,167

(22) PCT Filed: Sep. 12, 2018

(86) PCT No.: PCT/CN2018/105257
§ 371 (c)(1),
(2) Date: Sep. 26, 2021

(87) PCT Pub. No.: WO2020/037737
PCT Pub. Date: Feb. 27, 2020

(65) Prior Publication Data
US 2022/0008492 A1 Jan. 13, 2022

(30) Foreign Application Priority Data
Aug. 20, 2018 (CN) .......................... 201810945379.1

(51) Int. Cl.
*A61K 36/16* (2006.01)

(52) U.S. Cl.
CPC ........ *A61K 36/16* (2013.01); *A61K 2236/333* (2013.01); *A61K 2236/37* (2013.01); *A61K 2236/51* (2013.01); *A61K 2236/53* (2013.01)

(58) Field of Classification Search
CPC .............. A61K 36/16; A61K 2236/333; A61K 2236/37; A61K 2236/51; A61K 2236/53
See application file for complete search history.

(56) References Cited

U.S. PATENT DOCUMENTS

2016/0038550 A1  2/2016  Kinzer

FOREIGN PATENT DOCUMENTS

| CN | 101596222 A | 12/2009 |
| CN | 108785336 A | 11/2018 |
| WO | WO 9947148 A1 | 9/1999 |

OTHER PUBLICATIONS

English translation of WO1999047148 from Innovation Q. (Year: 1999).*

* cited by examiner

*Primary Examiner* — Trevor Love
(74) *Attorney, Agent, or Firm* — IPRTOP LLC

(57) ABSTRACT

The present disclosure provides a *Ginkgo biloba* ketone ester bulk drug. The present disclosure further provides a method for preparing *Ginkgo biloba* ketone ester bulk drug and use thereof. The present disclosure provides a *Ginkgo biloba* ketone ester and a preparation method thereof. Through optimized preparation operations and conditions, high-quality *Ginkgo biloba* ketone ester bulk drug can be obtained. Compared with the *Ginkgo biloba* ketone ester prepared by traditional methods, the *Ginkgo biloba* ketone ester of the present disclosure has stable quality, low unqualified rate, and good consistency of different batches of bulk drugs.

4 Claims, 1 Drawing Sheet

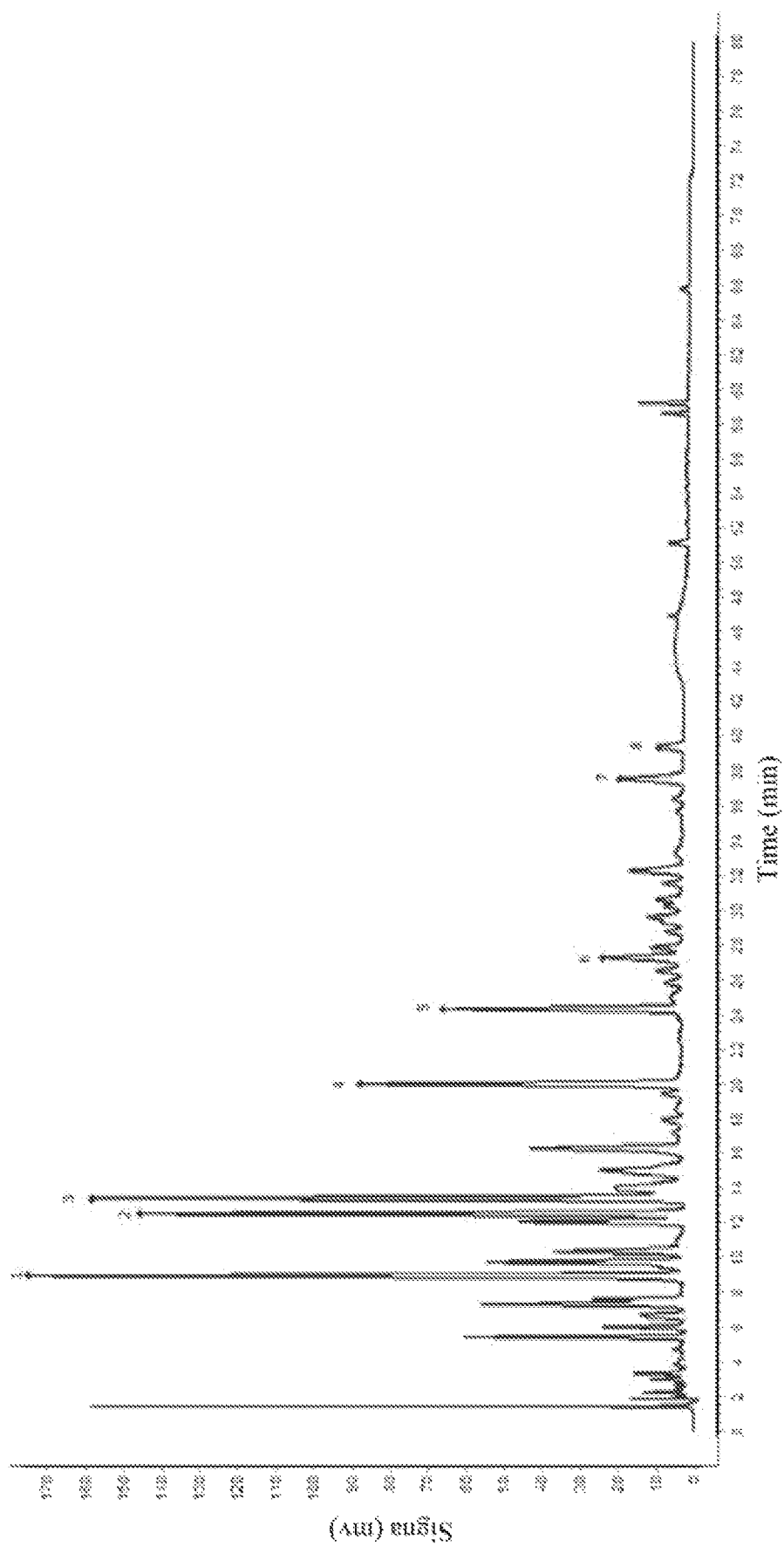

EXTRACT OF GINKGO BILOBA LEAVES AND PREPARATION METHOD THEREFOR

CROSS REFERENCE TO RELATED PATENT APPLICATION

The present application is the US national stage of PCT/CN2018/105257 filed on Sep. 12, 2018, which claims the priority of the Chinese patent application No. 201810945379.1 filed on Aug. 20, 2018, which application is incorporated herein by reference.

TECHNICAL FIELD

The present disclosure relates to the technical field of traditional Chinese medicines, and in particular, to a Ginkgo biloba ketone ester and preparation method thereof.

BACKGROUND

With the increasing aging of the population in China, people's awareness of prevention and treatment of cardiovascular and cerebrovascular diseases is gradually increasing. Ginkgo biloba leaves are the dry leaves of Ginkgo biloba which are sweet, bitter, astringent and calming, and belongs to heart and lung channels. According to the records of "Chinese Traditional Medicine Records", Ginkgo biloba leaves can "astringe Lung Qi, relieve cough and asthma, and stop whites and turbidity". Ginkgo biloba ketone ester, as raw material, is a Ginkgo biloba leaf extract product developed in China. It is an extract from the dried leaves of Ginkgo Biloba L, a plant of the Ginkgo family. Ginkgo biloba ketone ester is a brown-yellow to yellow-brown powder with a unique aroma and bitter taste. Ginkgo biloba ketone ester is mainly used for the treatment of cardiovascular and cerebrovascular diseases and neurological diseases with significant curative effects. Due to the remarkable curative effect of Ginkgo biloba ketone esters, adulteration is serious in the production process of relevant products on the market. For example, flavonoid aglycones such as quercetin are added to increase the determined content of total flavonol glycosides, and Ginkgo biloba root bark extract is added to improve lactone content. Due to the existing counterfeit Ginkgo biloba ketone ester products in the market, it is necessary to conduct in-depth research on Ginkgo biloba ketone ester to make the product quality more stable, and it's also necessary to establish manufacturing standards to normalize production technology and prevent adulteration products.

SUMMARY

The present disclosure provides a Ginkgo biloba ketone ester and preparation method thereof, to solve the problem that the traditional Ginkgo biloba ketone ester bulk drug is unstable in quality and low in qualification rate.

The first aspect of the present disclosure provides a Ginkgo biloba ketone ester, which is obtained from Ginkgo biloba leaves by alcohol extraction and meets the following conditions:

1) the content of rutin ($C_{27}H_{30}O_{16}$, CAS number 153-18-4) is less than or equal to 4.0%;
2) the content of quercetin ($C_{15}H_{10}O_7$, CAS number 117-39-5) is less than or equal to 0.4%;
3) the content of bilobalide ($C_{15}H_{18}O_8$, CAS number 33570-04-6) is 2.6-4.8%;
4) the content of Ginkgolide J ($C_{20}H_{24}O_{10}$, CAS number 107438-79-9) is 0.1-0.5%;
5) the residual content of ethanol is less than or equal to 0.5%;
6) the content of biflavonoids is less than or equal to 0.02%, the biflavonoids include Amentoflavone ($C_{30}H_{18}O_{10}$, CAS number 1617-53-4), Bilobetin ($C_{31}H_{20}O_{10}$, CAS number: 521-32-4), and Ginkgetin ($C_{32}H_{22}O_{10}$, CAS number 481-46-9);
7) the content of Genistin (CAS number 529-59-9) is 0, and the content of Ginkgolide M (CAS number 15291-78-8) is 0.

The above-mentioned alcohol extraction refers to a method for extracting Ginkgo biloba ketone esters from Ginkgo biloba leaves with alcohol solvents.

Preferably, the content of the rutin is less than or equal to 3.2%.

Preferably, the content of the quercetin is less than or equal to 0.38%.

Preferably, the residual content of ethanol is less than or equal to 0.2%.

Preferably, the content of the bilobalide is 3.6-4.8%.

Preferably, the content of the Ginkgolide J is 0.3-0.5%.

Preferably, the content of the biflavonoids is less than or equal to 0.01%.

Preferably, the content of total flavonoids in the Ginkgo biloba ketone ester is 44.0-55.0% by using rutin ($C_{27}H_{30}O_{16}$) as a standard sample.

More preferably, the content of total flavonoids in the Ginkgo biloba ketone ester is 49.0-55.0% by using rutin as a standard sample. The content of total flavonoids in the Ginkgo biloba ketone ester is calculated according to General Rules 0401 in Chinese Pharmacopoeia (2015 Edition) Volume IV.

Preferably, the content of terpene lactones in the Ginkgo biloba ketone ester is 6.0-12.0% calculated by the total contents of bilobalide ($C_{15}H_{18}O_8$, CAS number 33570-04-6), Ginkgolide A ($C_{20}H_{24}O_9$, CAS number 15291-75-5), Ginkgolide B ($C_{20}H_{24}O_{10}$, CAS number 15291-77-7) and Ginkgolide C ($C_{20}H_{24}O_{11}$, CAS number 15291-76-6). The content of terpene lactones is calculated as dry products.

More preferably, the content of terpene lactones in the Ginkgo biloba ketone ester is 9.0-12.0% calculated by the total contents of bilobalide, Ginkgolide A, Ginkgolide B and Ginkgolide C.

Preferably, the content of total Ginkgolic acid in the Ginkgo biloba ketone ester is less than or equal to 5 mg/kg.

More preferably, the content of total Ginkgolic acid in the Ginkgo biloba ketone ester is less than or equal to 1 mg/kg.

More preferably, the total Ginkgolic acids in the Ginkgo biloba ketone ester is characterized by the total contents of Ginkgolic acid C13:0 ($C_{20}H_{32}O_3$, CAS number 20261-38-5), Ginkgolic acid C15:1 ($C_{22}H_{34}O_3$, CAS number 22910-60-7), and Ginkgolic acid C17:1 ($C_{24}H_{38}O_3$, CAS number 111047-30-4). The content of total Ginkgolic acids is calculated according to General Rules 0512 and 0431 in Chinese Pharmacopoeia (2015 Edition) Volume IV.

Preferably, the content of total flavonol glycosides in the Ginkgo biloba ketone ester is 24.0-35.0%. The content of total flavonol glycosides is calculated as dry products.

More preferably, the content of total flavonol glycosides in the Ginkgo biloba ketone ester is 30.0-35.0%.

More preferably, the total flavonol glycosides are mainly glycosides formed by quercetin, kaempferide and isorhamnetin as aglycons, and contain free quercetin, kaempferide and isorhamnetin.

More preferably, the content of total flavonol glycosides is calculated according to formula (1): content of total flavonol glycosides=(quercetin content+kaempferide content+isorhamnetin content)×2.51.

Preferably, the chromatographic peak area ratio of quercetin to kaempferide ($C_{16}H_{12}O_6$, CAS number 491-54-3) in the *Ginkgo biloba* ketone ester is 0.8-1.2, and the chromatographic peak area ratio of isorhamnetin ($C_{16}H_{12}O_7$, CAS number 207-545-5480-19-3) to quercetin is more than 0.15. The three aglycones (quercetin, kaempferide and isorhamnetin) produced after the hydrolysis of Ginkgo flavonoids in the *Ginkgo biloba* ketone ester have a certain proportional relationship, which to some extent may reflect and determine whether the raw materials and production processes are normalized or not, and may also be used to control product quality. The chromatographic peak area ratios of quercetin to kaempferol and isorhamnetin to quercetin are calculated according to the traditional methods for determinating total flavonoid glycosides.

Preferably, the fingerprint spectrum of the *Ginkgo biloba* ketone ester includes four common fingerprint peaks as shown in FIG. 1: the peak 1 is the fingerprint peak of rutin, the peak 6 is the fingerprint peak of quercetin, the peak 7 is the fingerprint peak of kaempferide, and the peak 8 is the fingerprint peak of isorhamnetin.

Preferably, the similarity between the fingerprint spectrum of the *Ginkgo biloba* ketone ester and the chromatogram of the test product is greater than or equal to 0.90. The similarity between the fingerprint spectra of test products and *Ginkgo biloba* ketone ester is calculated and compared according to "Similarity Evaluation System for Chromatographic Fingerprint of Traditional Chinese Medicine" (version 2.0).

Preferably, the content of water in the *Ginkgo biloba* ketone ester is less than or equal to 5.0%. The water is calculated according to the second method of General Rules 0832 in Chinese Pharmacopoeia (2015 Edition) Volume IV.

Preferably, the content of ignition residue in the *Ginkgo biloba* ketone ester is less than or equal to 0.5%. The ignition residue is calculated according to Appendix IX J of the Chinese Pharmacopoeia (2010 edition) Volume I.

More preferably, the content of ignition residue in the *Ginkgo biloba* ketone ester is less than or equal to 0.2%.

Preferably, the content of cyclohexane residue in the *Ginkgo biloba* ketone ester is less than or equal to 0.002%. The content of cyclohexane residue is calculated according to the second method of General Rules 0861 in Chinese Pharmacopoeia (2015 Edition) Volume IV.

More preferably, the content of cyclohexane residue in the *Ginkgo biloba* ketone ester is less than or equal to 0.001%.

The contents of rutin, quercetin, bilobalide, Ginkgolide J, total flavonol glycoside and terpene lactone, and the fingerprint spectrum of *Ginkgo biloba* ketone ester in the above *Ginkgo biloba* ketone ester are determined by high performance liquid chromatography (HPLC) in General Rules 0512 in Chinese Pharmacopoeia (2015 Edition) Volume IV. The contents of diflavonoid, total Ginkgolic acids, Ginkgolide M and genistin are determined according to high performance liquid chromatography-mass spectrometry (HPLC-MS).

Preferably, in the *Ginkgo biloba* ketone ester, the content of lead (Pb) is less than or equal to 3.0 mg/kg, the content of cadmium (Cd) is less than or equal to 0.2 mg/kg, the content of arsenic (As) is less than or equal to 2.0 mg/kg, the content of mercury (Hg) is less than or equal to 0.1 mg/kg, and the content of copper (Cu) is less than or equal to 20 mg/kg.

The content of lead, cadmium, arsenic, mercury, and copper in the *Ginkgo biloba* ketone ester is determined according to the lead, cadmium, arsenic, mercury, and copper determination method described in General Rules 2321 in Chinese Pharmacopoeia (2015 Edition).

Preferably, the contents of pesticide residues in the *Ginkgo biloba* ketone ester are as follows: in the *Ginkgo biloba* ketone ester, total BHC (CAS No. 58-89-9)≤content 0.2 mg/kg, total DDT (CAS No. 50-29-3) content≤0.2 mg/kg, pentachloronitrobenzene (CAS No. 82-68-8) content≤0.1 mg/kg, dichlorvos (CAS No. 62-73-7) content≤0.5 mg/kg, methamidophos (CAS No. 10265-92-6) content≤0.05 mg/kg, acephate (CAS No. 30560-19-1) content≤0.1 mg/kg, ethion (CAS No. 563-12-2) content≤0.5 mg/kg, omethoate (CAS No. 1113-02-6) content≤0.05 mg/kg, diazinon (CAS No. 333-41-5) content methidathion (CAS No. 950-37-8) content≤0.05 mg/kg, monocrotophos (CAS No. 6923-22-4) content≤0.1 mg/kg, dimethoate (CAS No. 60-51-5) content≤0.1 mg/kg, parathion-methy (CAS No. 298-00-0) content≤0.1 mg/kg, cypermethrin (CAS No. 52315-07-8) content≤1 mg/kg, fenvalerate (CAS No. 51630-58-1) content≤0.5 mg/kg, deltamethrin (CAS No. 52918-63-5) content≤50.5 mg/kg.

The content of the above-mentioned pesticide residues in the *Ginkgo biloba* ketone ester is determined according to the pesticide residue determination method described in General Rules 2341 in Chinese Pharmacopoeia (2015 Edition) Volume IV.

Preferably, in each 1000 g of the *Ginkgo biloba* ketone ester, the total contents of aflatoxins is ≤4 μg, and the content of aflatoxin B1 is ≤2 μg. The aflatoxins include aflatoxin G2, aflatoxin G1, aflatoxin B2, and aflatoxin B1.

The content of aflatoxins in the *Ginkgo biloba* ketone ester is determined according to the aflatoxin determination method described in General Rules 2351 in Chinese Pharmacopoeia (2015 Edition) Volume IV.

Preferably, the *Ginkgo biloba* leaves are dried *Ginkgo biloba* nursery leaves. The *Ginkgo biloba* nursery leaves are leaves of non-adult Ginkgo trees, which are planted for the purpose of collecting *Ginkgo biloba* leaves.

More preferably, the drying conditions are: the drying temperature is 140-160° C., and the drying time is 6-15 minutes.

More preferably, the *Ginkgo biloba* nursery leaves meet the following requirements:
a) the content of total flavonol glycosides is greater than or equal to 0.85%;
b) The content of terpene lactones is greater than or equal to 0.40%;
c) the content of total ash is less than or equal to 10.0%;
d) the content of acid-insoluble ash is less than or equal to 2.0%;
e) the content of extractum is greater than or equal to 25.0%;
f) the chromatographic peak area ratio of quercetin to kaempferide is 0.65-1.2, and the chromatographic peak area ratio of isorhamnetin to quercetin is more than 0.15;
g) the content of impurity is less than or equal to 2.0%;
h) the content of water is less than or equal to 12.0%;
i) the content of sulfur dioxide residue is less than or equal to 150 mg/kg.

The definitions of the total flavonol glycosides and terpene lactones in the *Ginkgo biloba* nursery leaves are the same as those of *Ginkgo biloba* ketone ester mentioned above. The definition of the chromatographic peak area ratio of flavonoid aglycones in the *Ginkgo biloba* nursery leaves (that is, the chromatographic peak area ratio among quercetin, kaempferide and isorhamnetin) is the same as that of the above-mentioned *Ginkgo biloba* ketone ester.

The contents of total ash and acid-insoluble ash in the *Ginkgo biloba* nursery leaves are determined according to the ash determination method described in General Rules 2302 in Chinese Pharmacopoeia (2015 Edition) Volume IV. The content of extractum in the *Ginkgo biloba* nursery leaves is determined according to the extractum determination method described in General Rules 2201 in Chinese Pharmacopoeia (2015 Edition) Volume IV. The content of impurity in the *Ginkgo biloba* nursery leaves is determined according to the impurity determination method described in General Rules 2301 in Chinese Pharmacopoeia (2015 Edition) Volume IV. The content of water in the *Ginkgo biloba* nursery leaves is determined according to the water determination method described in General Rules 0832 in Chinese Pharmacopoeia (2015 Edition) Volume IV. The content of sulfur dioxide residue in the *Ginkgo biloba* nursery leaves is determined according to the sulfur dioxide residue determination method described in General Rules 2331 in Chinese Pharmacopoeia (2015 Edition) Volume IV.

The above % are all mass percentages.

The second aspect of the present disclosure provides a method for preparing *Ginkgo biloba* ketone ester, which includes the following operations:
1) adding ethanol aqueous solution to crushed *Ginkgo biloba* leaves, heating at reflux for extraction, and then obtaining a filtrate by filtration;
2) concentrating the filtrate and performing water-sedimentation, centrifuging the supernatant to obtain the centrifugal liquid;
3) loading the centrifugal liquid onto a macroporous resin column, then washing with water and eluting with solvent to obtain a first eluent; the first eluent includes a low-concentration-solvent first eluent and a high-concentration-solvent first eluent;
4) loading the low-concentration-solvent first eluent onto a polyamide column, then washing with water and eluting with ethanol to obtain a second eluent;
5) combining and concentrating the second eluent with the high-concentration-solvent first eluent, and then extracting, drying, crushing, sieving, and mixing to obtain the desired *Ginkgo biloba* ketone ester.

Preferably, in operation 1), the crushed *Ginkgo biloba* leaves are obtained by crushing *Ginkgo biloba* leaves.

Preferably, in operation 1), the obtaining of the filtrate includes the following:
A) adding 60% ethanol aqueous solution to crushed *Ginkgo biloba* leaves, heating at reflux for extraction, and then obtaining a first filtrate by filtration;
B) adding water to the residual medicine residue after the filtration in operation A), heating at reflux for extraction, and then obtaining a second filtrate by filtration;
C) combining and concentrating into a thick paste the second filtrate in operation B) and the first filtrate in operation A), dissolving, standing to cool, and filtering to obtain the desired filtrate.

More preferably, in operation A), the conditions of the heating at reflux for extraction are: 2 times of extraction; 3 hours for each extraction time.

More preferably, in operation B), the conditions of the heating at reflux for extraction are: 1 time of extraction; 0.5 hours for each extraction time.

More preferably, in operation B), the water is purified water.

More preferably, in operation C), the combining and concentrating is selected from one of a method of concentrating after combining or a method of combining after concentrating. The method of concentrating after combining is to combine the second filtrate with the first filtrate and then concentrate. The method of combining after concentrating is to concentrate the first filtrate first, and then combine with the second filtrate and continue to concentrate.

More preferably, in operation C), the dissolving is the dissolving by using hot water. The hot water is purified water which has been heated to 60-100° C.

Preferably, in operation 2), the filtrate is concentrated to have no alcohol smell.

Preferably, in operation 2), the relative density of the concentrated filtrate is 1.04-1.08.

Preferably, in operation 2), the purified water added in the water-sedimentation is 1.5-2.5 times the amount of the *Ginkgo biloba* leaf powder. Specifically, that the purified water added is 1.5-2.5 times the amount of the *Ginkgo biloba* leaf powder means that 1.5-2.5 ml of purified water is added to each 1 g of the *Ginkgo biloba* leaf powder.

Preferably, in operation 2), the water-sedimentation is the interlayer cooling in 5-7° C. cooling water for 12-24 hours.

Preferably, in operation 2), the centrifugation conditions are as follows: the centrifugal speed is 13,000-15,000 rpm, and the centrifugal time per 3-5 L of supernatant is 0.75-1.25 min.

More preferably, the centrifugation conditions are as follows: the centrifugal speed is 14,000 rpm, and the centrifugal time per 3-5 L of supernatant is 1.00 min.

In operation 2), the above-mentioned concentration, water-sedimentation and centrifugation can ensure the optimization of the quality conditions of the *Ginkgo biloba* ketone ester prepared by the present disclosure, so that the quality of the *Ginkgo biloba* ketone ester is better.

Preferably, in operation 3), the washing with water is forward-washing with purified water for 1-2 hours first, and then backwashing for 0.5-1.5 hours. The washing with water can ensure the optimization of quality conditions such as Ginkgolic acids and ignition residue in the *Ginkgo biloba* ketone ester prepared by the present disclosure, so that the quality of the *Ginkgo biloba* ketone ester is better.

More preferably, the washing with water is forward-washing with purified water for 1.5 hours first, and then backwashing for 1 hour.

Preferably, in operation 3), the eluting with solvent is eluting with 18% ethanol aqueous solution, 30% ethanol aqueous solution and 50% ethanol aqueous solution in sequence to obtain 18% ethanol eluent, 30% ethanol eluent and 50% ethanol eluent, respectively.

Preferably, in operation 3), the high-concentration-solvent first eluent is a 50% ethanol eluent.

Preferably, in operation 3), the low-concentration-solvent first eluent is a combined solution of an 18% ethanol eluent and a 30% ethanol eluent.

Preferably, in operation 4), the washing with water is forward-washing by using purified water 0.5-2 times the volume of the polyamide column. More preferably, the washing with water is forward-washing by using purified water 1 time the volume of the polyamide column. The washing with water is capable of further removing impurities, including Ginkgolic acids, from the *Ginkgo biloba* ketone ester.

Preferably, in operation 4), the low-concentration-solvent first eluent is concentrated to have no alcohol smell before being loaded to the polyamide column.

Preferably, in operation 4), the second eluent is an ethanol eluent.

Preferably, in operation 5), the combining and concentrating is selected from one of a method of concentrating after combining or a method of combining after concentrating. The method of concentrating after combining is to combine the second eluent with the high-concentration-solvent first eluent and then concentrate. The method of combining after concentrating is to concentrate the high-concentration-solvent first eluent first, and then combine with the second eluent and continue to concentrate.

Preferably, in operation 5), the second eluent and the high-concentration-solvent first eluent are concentrated to have no alcohol smell.

Preferably, in operation 5), the extracting is carried out using cyclohexane as a solvent. After the extracting, the cyclohexane extract is discarded.

Preferably, in operation 5), the drying is selected from spray drying or vacuum drying.

More preferably, before the vacuum drying, the concentrated solution needs to be concentrated into a thick paste.

Preferably, in operation 5), the sieving is by passing through an 80-100 mesh sieve. More preferably, the sieving is by passing through a 90-100 mesh sieve. Most preferably, the sieving is by passing through a 100 mesh sieve. The sieving can ensure that the particle size of the *Ginkgo biloba* ketone ester bulk drug prepared by the present disclosure is finer, so that the quality of the *Ginkgo biloba* ketone ester is better.

Preferably, in operation 5), the conditions for the mixing are: the mixing equipment is a total mixer; the mixing speed is 10-12 rpm; the mixing time is 1.5-2.5 hours. The mixing can ensure better uniformity of the *Ginkgo biloba* ketone ester bulk drug prepared by the present disclosure, so that the quality of the *Ginkgo biloba* ketone ester is better.

More preferably, the conditions for the mixing are: the mixing equipment is a total mixer; the mixing speed is 11 rpm; the mixing time is 2 hours.

The third aspect of the present disclosure provides the use of the method for preparing *Ginkgo biloba* ketone ester in the preparation of *Ginkgo biloba* ketone ester.

The fourth aspect of the present disclosure provides a *Ginkgo biloba* ketone ester preparation, which is prepared from the above *Ginkgo biloba* ketone ester bulk drug.

Preferably, the preparation is selected from one of tablets, capsules, granules, pills, powders, oral liquids, injections or external pharmaceutical preparations.

As mentioned above, the present disclosure provides a *Ginkgo biloba* ketone ester and a preparation method thereof. Through optimized preparation operations and conditions, high-quality *Ginkgo biloba* ketone ester bulk drug can be obtained. Compared with the *Ginkgo biloba* ketone ester prepared by traditional methods, the *Ginkgo biloba* ketone ester of the present disclosure has stable quality, low unqualified rate, and good consistency of different batches of bulk drugs. Meanwhile, the *Ginkgo biloba* ketone ester bulk drug prepared by the method of the present disclosure is used to prepare preparations such as tablets, capsules, granules, pills, powders, oral liquids, injections or external pharmaceutical preparations, etc., and has excellent stability and consistency.

BRIEF DESCRIPTION OF THE DRAWINGS

FIG. 1 shows the fingerprint spectrum of the *Ginkgo biloba* ketone ester according to the present disclosure; in the fingerprint spectrum, 1: rutin; 6: quercetin; 7: kaempferide; 8: isorhamnetin.

DETAILED DESCRIPTION OF THE PREFERRED EMBODIMENTS

The present disclosure is further described below with reference to specific embodiments. It should be understood that the embodiments are just for describing the present disclosure instead of limiting the scope of the present disclosure.

The embodiments of the present disclosure will be described below. Those skilled in the art can easily understand other advantages and effects of the present disclosure according to contents disclosed by the specification. The present disclosure can also be implemented or applied through other different exemplary embodiments. Various modifications or changes can also be made to all details in the specification based on different points of view and applications without departing from the spirit of the present disclosure.

It should be noted that processing equipment or devices not specifically noted in the following embodiments are all conventional equipment or devices in the field. All pressure values and ranges refer to relative pressures. The reagents used below are all conventional reagents in the field. The instruments used below are all conventional instruments in the field.

In addition, it should be understood that one or more method steps mentioned in the present disclosure are not exclusive of other method steps that may exist before or after the combined steps or that other method steps may be inserted between these explicitly mentioned steps, unless otherwise stated; it should also be understood that the combined connection relationship between one or more equipment/devices mentioned in the present disclosure does not exclude that there may be other equipment/devices before or after the combined equipment/devices or that other equipment/devices may be inserted between these explicitly mentioned equipment/devices, unless otherwise stated. Moreover, unless otherwise stated, the numbering of each method step is only a convenient tool for identifying each method step, and is not intended to limit the order of each method step or to limit the scope of the present disclosure. The change or adjustment of the relative relationship shall also be regarded as the scope in which the present disclosure may be implemented without substantially changing the technical content.

Embodiment 1

Dried *Ginkgo biloba* nursery leaves are crushed to obtain crushed *Ginkgo biloba* leaves. Adding 60% ethanol aqueous solution to the crushed *Ginkgo biloba* leaves, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining and concentrating the second filtrate and the first filtrate into a thick paste. The combining and concentrating may be conducted by concentrating after combining or combining after concentrating. Dissolving in purified water which has been heated to 60-100° C., standing to cool, and filtering to obtain a filtrate. Concentrating the filtrate to a relative density of 1.04-1.08 and without alcohol smell, adding purified water that is 1.5-2.5 times the amount of the *Ginkgo biloba* leaf powder, cooling in interlayer in 5-7° C. cooling water for 12-24 h, and centrifuging the supernatant at a speed of 14,000 rpm to obtain a centrifugal liquid. Loading the centrifugal liquid onto a macroporous resin column, forward-washing with purified water for 1.5 hours first, and then backwashing for 1 hour. Eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, forward-washing with purified water that is 1 times the volume of the polyamide column, and then eluting with ethanol to obtain an ethanol eluate, which is the second eluate. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products, passing through a 100-mesh sieve, and mixing in a total mixer at a speed of 11 rpm for 2 hours to obtain the desired *Ginkgo biloba* ketone ester Sample 1 #.

Control Example 1

Conventional *Ginkgo biloba* leaves are crushed to obtain crushed *Ginkgo biloba* leaves. Adding 60% ethanol aqueous solution to the crushed *Ginkgo biloba* leaves, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining the second filtrate and the first filtrate into a thick paste. The combining and concentrating may be conducted by concentrating after combining or combining after concentrating. Dissolving in purified water which has been heated to 60-100° C., standing to cool, and filtering to obtain a filtrate. Loading the filtrate onto a macroporous resin column, eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, eluting with ethanol to obtain an ethanol eluate, which is the second eluate. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products to obtain the desired *Ginkgo biloba* ketone ester Control Sample 1*.

Control Example 2

Conventional *Ginkgo biloba* leaves, *Ginkgo biloba* root bark and Fructus Sophorae are crushed to obtain crushed *Ginkgo biloba*. Adding 60% ethanol aqueous solution to the crushed *Ginkgo biloba*, extracting twice by heating at reflux, each for 3 hours, and obtaining a first filtrate by filtration. Then, adding water to the filtered medicine residue left after the filtration, extracting for one time by heating at reflux with the extraction time of 0.5 hours, and then obtaining a second filtrate by filtration. Combining and concentrating the second filtrate and the first filtrate into a thick paste. The combining and concentrating may be conducted by concentrating after combining or combining after concentrating. Dissolving in purified water which has been heated to 60-100° C., standing to cool, and filtering to obtain a filtrate. Loading the filtrate onto a macroporous resin column, eluting with 18% ethanol aqueous solution, 30% ethanol aqueous solution and 50% ethanol aqueous solution in sequence to obtain 18% ethanol eluent, 30% ethanol eluent and 50% ethanol eluent, respectively, which are the first eluents. In the first eluents, the 50% ethanol eluent is the high-concentration-solvent first eluent, and the combined solution of the 18% ethanol eluent and the 30% ethanol eluent is the low-concentration-solvent first eluent. The low-concentration-solvent first eluent is then concentrated to have no alcohol smell. Loading the low-concentration-solvent first eluent onto a polyamide column, eluting with ethanol to obtain an ethanol eluate, which is the second eluate. Combining and concentrating the second eluent and the high-concentration-solvent first eluent until there is no alcohol smell. The combining and concentrating may be conducted by concentrating after combining or combining after concentrating. After the concentrate is extracted with cyclohexane, the cyclohexane extract is discarded. Then, spray-drying the concentrated solution, or concentrating the concentrated solution into a thick paste and vacuum-drying the thick paste. Pulverizing the dried products to obtain the desired *Ginkgo biloba* ketone ester Control Sample 2*.

Embodiment 2

Respectively taking 0.1 g of the powder from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the powder, placing the powder in a conical flask with stopper, precisely adding 10 ml of a mixed solution of 70% methanol-70% ethanol (1:1), and extracting by shaking (500 times per minute) for 30 minutes. Taking out the solution for centrifugation to obtain the supernatant (or, filtering the solution to obtain the subsequent filtrates), to obtain the test product solutions A1, A2 and A3.

At the same time, taking appropriate amounts of rutin reference substance and quercetin reference substance, precisely weighing the reference substances. The reference substances are added with methanol to prepare a mixed solution containing 250 µg of rutin and 25 µg of quercetin per 1 ml, to obtain the reference solution.

Precisely pipetting 10 µl from the test product solutions A1, A2, A3 and the reference solution, respectively, which are then determined by high performance liquid chromatography (HPLC) in General Rules 0512 in Chinese Pharmacopoeia (2015 Edition) Volume IV. The conditions of the high-performance liquid chromatography are: octadecylsilane chemically bonded silica gel serves as a filler; acetonitrile serves as mobile phase A, and 0.4% phosphoric acid solution serves as mobile phase B. Gradient elution is performed according to the specification in Table 1 below; the detection wavelength is 400 nm. The number of theoretical plates calculated by the rutin peak is no less than 8000.

TABLE 1

| Time (minutes) | Mobile phase A (%) | Mobile phase B (%) |
|---|---|---|
| 0~35 | 15 | 85 |
| 35~80 | 20 | 80 |

The determination result shows that in Ginkgo biloba ketone ester Sample 1#, the content of rutin is 3.0%, and the value is ≤3.2%; the content of quercetin is 0.36%, and the value is <0.38%. In Ginkgo biloba ketone ester Control Sample 1*, the content of rutin is 3.5%, and the value is ≤4.0%; the content of quercetin is 0.39%, and the value is <0.4%. In Ginkgo biloba ketone ester Control Sample 2*, the content of rutin is 5.5%, and the value is >4.0%; the content of quercetin is 0.59%, and the value is >0.4%. It can be seen from the above content values that the contents of rutin and quercetin in Ginkgo biloba ketone ester Sample 1# and Ginkgo biloba ketone ester Control Sample 1* are within the specified value range, indicating that there are no adulterated foreign substances, the production process is normal, and the product quality is good. Due to the operations such as washing in the preparation method, the contents of rutin and quercetin in Ginkgo biloba ketone ester Sample 1# are all lower than that of Ginkgo biloba ketone ester Control Sample 1*, indicating that the product quality of Ginkgo biloba ketone ester Sample 1# is better than that of Ginkgo biloba ketone ester Control Sample 1*. The contents of rutin and quercetin in Ginkgo biloba ketone ester Control Sample 2* exceed the specified value range, indicating that there may be adulterated foreign substances, and the product quality is poor.

Embodiment 3

Respectively taking 1 g of the Ginkgo biloba ketone ester Sample 1# (prepared in Embodiment 1), the Ginkgo biloba ketone ester Control Sample 1* and 2* (prepared in Control Examples 1 and 2, respectively), and spray-drying the samples. Drying the samples in a vacuum oven at a temperature of ≤80° for 2 hours; or concentrating a liquid extract to a relative density of 1.2, and then drying with an inlet air temperature of 160-165° and an outlet air temperature of 95-100°.

The determination result shows that in Ginkgo biloba ketone ester Sample 1#, the content of ethanol residue is 0.18%, and the value is <0.2%. In Ginkgo biloba ketone ester Control Sample 1*, the content of ethanol residue is 0.43%, and the value is <0.5%. In Ginkgo biloba ketone ester Control Sample 2*, the content of ethanol residue is 0.47%, and the value is <0.5%. It can be seen from the above contents that the ethanol residues in Ginkgo biloba ketone ester Sample 1#, Ginkgo biloba ketone ester Control Sample 1* and 2* all meet the control requirements. However, Ginkgo biloba ketone ester Sample 1# has the least residual ethanol and the best quality. Ginkgo biloba ketone ester Control Sample 1* and 2* have almost the same amount of residual ethanol, but the amount of residual ethanol is higher than that of Ginkgo biloba ketone ester Sample 1#, therefore has inferior quality.

Embodiment 4

Respectively taking 0.1 g of powder from the Ginkgo biloba ketone ester Sample 1# (prepared in Embodiment 1), the Ginkgo biloba ketone ester Control Sample 1* and 2* (prepared in Control Examples 1 and 2, respectively), precisely weighing the powder, placing the powder in a 50 ml centrifuge tube with a stopper, adding 15 ml of 30% ethanol, shaking well, adding 20 ml of diethyl ether, shaking well, standing for a while, carefully opening the lid, tightening the lid after deflation, vortexing (3000 times per minute) for 1 minute, centrifuging for 10 minutes (4000 rpm), separating the supernatant. Adding diethyl ether to the residue, repeating the above operations 3 times, 15 ml of diethyl ether each time. Combining the four diethyl ether solutions, concentrating under reduced pressure to near dryness (do not evaporate to dryness), adding a proper amount of methanol and dissolving by ultrasonic, and completely transferring to a 5 ml measuring flask. Centrifuging to obtain the supernatant (or passing through a 0.45 µm filter membrane to obtain the subsequent filtrates), to obtain the test product solutions B1, B2 and B3.

At the same time, taking appropriate amounts of bilobalide reference substance, Ginkgolide A reference substance, Ginkgolide B reference substance, Ginkgolide C reference substance and Ginkgolide J reference substance, and precisely weighing the reference substances. The reference substances are added with methanol to prepare mixed solutions each containing 1.0 mg, 0.3 mg, 0.7 mg and 0.4 mg of each reference substance per 1 ml, which is the reference solution.

Precisely pipetting 5 µl and 10 µl from the reference solution, and 10 µl from the test product solutions B1, B2 and B3, respectively, which are then determined by high performance liquid chromatography (HPLC) in General Rules 0512 in Chinese Pharmacopoeia (2015 Edition) Volume IV. The contents of bilobalide, Ginkgolide A, Ginkgolide B, Ginkgolide C and Ginkgolide J are calculated by using an external standard two-point logarithmic equation. The conditions of the high-performance liquid chromatography are: octadecylsilane chemically bonded silica gel serves as a filler; methanol serves as mobile phase A, and water serves as mobile phase B. Gradient elution is performed according to the specification in Table 2 below; the detection is performed by an evaporative light scattering detector. The number of theoretical plates calculated by the bilobalide peak is no less than 10000.

TABLE 2

| Time (minutes) | Mobile phase A (%) | Mobile phase B (%) |
|---|---|---|
| 0~15 | 30 | 70 |
| 15~30 | 40 | 60 |

The determination shows that the contents of terpene lactones in the Ginkgo biloba ketone ester Sample 1# and

*Ginkgo biloba* ketone ester Control Sample 1* are calculated as dry products, and are calculated by the total contents of bilobalide, Ginkgolide A, Ginkgolide B and Ginkgolide C. The contents of terpene lactones in the *Ginkgo biloba* ketone ester Sample 1# and *Ginkgo biloba* ketone ester Control Sample 1* are 11.5% and 8.0%, respectively, which are within the specified data range of 6.0-12.0%. The content of terpene lactones in the *Ginkgo biloba* ketone ester Control Sample 2* is calculated as dry products, and is calculated by the total contents of bilobalide, Ginkgolide A, Ginkgolide B and Ginkgolide C. The content of terpene lactones in the *Ginkgo biloba* ketone ester Control Sample 2* is 4.3%, which is lower than the specified data range of 6.0-12.0%. Terpene lactones, as unique components in *Ginkgo biloba*, are the main effective components of *Ginkgo biloba* ketone ester preparation in blood-activating and stasis-eliminating as well as in the treatment of angina pectoris, coronary heart disease and cerebral arteriosclerosis. Therefore, terpene lactones need to be within a specified data range. It can be seen that the *Ginkgo biloba* ketone ester Control Sample 2* has a poor treatment effect. *Ginkgo biloba* ketone ester Sample 1# and *Ginkgo biloba* ketone ester Control Sample 1* both have good therapeutic effects. However, the content of terpene lactones in *Ginkgo biloba* ketone ester Sample 1# is higher, which is within a specified data range of 9.0-12.0%. Compared with *Ginkgo biloba* ketone ester Control Sample 1*, *Ginkgo biloba* ketone ester Sample 1# has a better therapeutic effect.

At the same time, the determination shows that the contents of bilobalide in the *Ginkgo biloba* ketone ester Sample 1# and *Ginkgo biloba* ketone ester Control Sample 1* are 4.6% and 2.8%, respectively, which are within a specified data range of 2.6-4.8%. The content of bilobalide in the *Ginkgo biloba* ketone ester Control Sample 2* is 1.8%, which is lower than the specified data range of 2.6-4.8%. Bilobalide gives *Ginkgo biloba* ketone ester an anti-PAF effect, as well as nutritional functions for nerves. Therefore, the *Ginkgo biloba* ketone ester Control Sample 2* has poor treatment effect. *Ginkgo biloba* ketone ester Sample 1# and *Ginkgo biloba* ketone ester Control Sample 1* both have good therapeutic effects. However, the content of bilobalide in *Ginkgo biloba* ketone ester Sample 1# is higher, which is within a specified data range of 3.6-4.8%. Compared with *Ginkgo biloba* ketone ester Control Sample 1*, *Ginkgo biloba* ketone ester Sample 1# has a better therapeutic effect.

In addition, the determination shows that the contents of Ginkgolide J in the *Ginkgo biloba* ketone ester Sample 1# and *Ginkgo biloba* ketone ester Control Sample 1* are 0.41% and 0.22%, respectively, which are within a specified data range of 0.1-0.5%. The content of Ginkgolide J in the *Ginkgo biloba* ketone ester Control Sample 2* is 0.05%, which is lower than the specified data range of 0.1-0.5%. Ginkgolide J also provides *Ginkgo biloba* ketone ester an anti-PAF effect. Therefore, the *Ginkgo biloba* ketone ester Control Sample 2* has a poor treatment effect. *Ginkgo biloba* ketone ester Control Sample 1* both have good therapeutic effects. However, the content of Ginkgolide J in *Ginkgo biloba* ketone ester Sample 1# is higher, which is within a specified data range of 0.3-0.5%. Compared with *Ginkgo biloba* ketone ester Control Sample 1*, *Ginkgo biloba* ketone ester Sample 1# has a better therapeutic effect.

Embodiment 5

Respectively taking 0.1 g of the powder from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the powder, extracting by ultrasonic with 5 mL ethanol for 10 min, centrifuging at 3000 rpm for 10 min, and then taking the supernatant. Repeating the above ultrasonic extraction 3 times. Combining the supernatant and bringing to volume with a 25 mL volumetric flask, to obtain the test product solutions C1, C2 and C3.

At the same time, respectively taking appropriate amounts of an amentoflavone reference substance, bilobetin reference substance and ginkgetin reference substance, and precisely weighing the reference substances. The reference substances are added with ethanol to prepare a mixed solution with a certain concentration of amentoflavone, bilobetin and ginkgetin, which is the reference solution.

Precisely pipetting 10 μl from the test product solutions C1, C2, C3 and the reference solution, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are: octadecylsilane chemically bonded silica gel serves as a filler; methanol-1% glacial acetic acid solution (90:10) serves as the mobile phase, eluting isocratically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode.

The determination shows that the contents of biflavonoids in *Ginkgo biloba* ketone ester Sample 1# and *Ginkgo biloba* ketone ester Control Sample 1* are 0.005% and 0.016%, respectively, that is, the total contents of amentoflavone, bilobetin and ginkgetin in *Ginkgo biloba* ketone ester Sample 1# and *Ginkgo biloba* ketone ester Control Sample 1* are all less than or equal to 0.02%. The content of biflavonoids in *Ginkgo biloba* ketone ester Control Sample 2* is 0.042%, that is, the total contents of amentoflavone, bilobetin and ginkgetin in *Ginkgo biloba* ketone ester Control Sample 2* is higher than 0.02%. The content of biflavonoids must be controlled due to their allergenicity. The content of biflavones in *Ginkgo biloba* ketone ester control sample 2*exceeds the limit, which will make patients more susceptible to allergy. The contents of biflavonoids in *Ginkgo biloba* ketone ester Sample 1# and *Ginkgo biloba* ketone ester Control Sample 1* are within the limit. However, *Ginkgo biloba* ketone ester Sample 1# has a lower biflavonoids content, which can reach 0.01% or less, and is less likely to cause sensitization.

Embodiment 6

Respectively taking 0.1 g of the powder from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the powder, extracting by ultrasonic with 5 mL of 50% methanol for 10 min, centrifuging at 3000 rpm for 10 min, and then taking the supernatant. Repeating the above ultrasonic extraction 3 times. Combining the supernatant and bringing to volume with a 25 mL volumetric flask, to obtain the test product solutions D1, D2 and D3.

At the same time, respectively taking appropriate amounts of genistin reference substance and Ginkgolide M reference substance, and precisely weighing the reference substances. The reference substances are added with methanol to prepare a mixed solution with a certain concentration of genistin and Ginkgolide M, which is the reference solution.

Precisely pipetting 10 μl from the test product solutions D1, D2, D3 and the reference solution, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are: octadecylsilane chemically bonded silica gel serves as a filler; methanol-1% glacial acetic acid solution (90:10) serves as the mobile phase, eluting isocratically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode.

It can be known from the determination that neither the *Ginkgo biloba* ketone ester Sample 1# nor the *Ginkgo biloba* ketone ester Control Sample 1* contains genistin or Ginkgolide M. However, the *Ginkgo biloba* ketone ester Control Sample 2* contains genistin and Ginkgolide M. Genistin is a component present in Fructus Sophorae, Ginkgolide M is a component present in *Ginkgo biloba* root bark, none of the above components are present in *Ginkgo biloba* leaves. Therefore, the detection of the above components in the *Ginkgo biloba* ketone ester Control Sample 2* means that foreign substances, such as Fructus Sophorae and *Ginkgo biloba* root bark, have been illegally adulterated into the *Ginkgo biloba* ketone ester Control Sample 2*. There are no adulterated foreign substances in *Ginkgo biloba* ketone ester Sample 1# and *Ginkgo biloba* ketone ester Control Sample 1*, indicating the product quality is good.

Embodiment 7

Taking 20 mg of the rutin reference substance, precisely weighing the rutin reference substance, placing the rutin reference substance in a 100 ml measuring flask, adding 70 ml of 70% ethanol, heating slightly in a water bath for dissolving, cooling, diluting to the mark with 70% ethanol, and shaking well to obtain the reference solution (containing 0.2 mg of anhydrous rutin per 1 ml).

Then, precisely measuring 0.2 ml, 0.4 ml, 0.6 ml, 0.8 ml, 1.0 ml and 1.2 ml of the reference solution, respectively placing the reference solution into 10 ml measuring flasks, respectively adding water to 3 ml, adding 2 ml acetic acid-sodium acetate buffer (pH4.5) and 2 ml 0.1 mol/L aluminum chloride solution, shaking well, adding 70% ethanol to the mark, and shaking well. The corresponding solution serves as the blank solution. The tests are performed according to ultraviolet-visible spectrophotometry (General Rules 0401 in Chinese Pharmacopoeia (2015 Edition) Volume IV). The absorbance is measured at 270 nm wavelength, and the standard curve is drawn with absorbance as ordinate and concentration as abscissa.

Respectively taking 25 mg from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the samples, placing the samples in 50 ml measuring flasks, dissolving and diluting to the mark with 70% ethanol, and shaking well. Precisely measuring 0.5 ml into a 10 ml measuring flask, adding water to 3 ml, adding 2 ml acetic acid-sodium acetate buffer (pH4.5) and 2 ml 0.1 mol/L aluminum chloride solution, shaking well, adding 70% ethanol to the mark, and shaking well. The tests are performed according to ultraviolet-visible spectrophotometry (General Rules 0401 in Chinese Pharmacopoeia (2015 Edition) Volume IV). The absorbance is measured at 270 nm wavelength. The equivalent weight of rutin in the test product solution is read from the standard curve, which is calculated to obtain the content of total flavonoids.

The determination shows that the contents of total flavonoids in *Ginkgo biloba* ketone ester Sample 1# and *Ginkgo biloba* ketone ester Control Sample 1* are 54.1% and 45.2% respectively by using rutin ($C_{27}H_{30}O_{16}$) as a standard sample, which is within a specified data range of 44.0-55.0%. The content of total flavonoids in *Ginkgo biloba* ketone ester Control Sample 2* is 38.1% by using rutin ($C_{27}H_{30}O_{16}$) as a standard sample, which is lower than the specified data range of 44.0-55.0%. Total flavonoids are active substances that contain free flavonoids besides total flavonoid glycosides. A certain amount of total flavonoids in *Ginkgo biloba* ketone ester endows *Ginkgo biloba* ketone ester with a good therapeutic effect. Therefore, the *Ginkgo biloba* ketone ester Control Sample 2* has a poor treatment effect. *Ginkgo biloba* ketone ester Sample 1# and *Ginkgo biloba* ketone ester Control Sample 1* both have good therapeutic effects. However, the content of total flavonoids in *Ginkgo biloba* ketone ester Sample 1# is higher, which is within a specified data range of 49.0-55.0%. Compared with *Ginkgo biloba* ketone ester Control Sample 1*, the *Ginkgo biloba* ketone ester Sample 1# has a better therapeutic effect.

Embodiment 8

Respectively taking 0.4 g of powder from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the powder, placing the powder in a conical flask with stopper, precisely adding 10 ml of methanol, weighing, treating with ultrasonic (power: 180 W, frequency: 42 kHz) for 20 minutes, cooling, weighing again, using methanol to make up for the weight loss. Filtering, and taking the subsequent filtrate to obtain test product solutions D1, D2 and D3.

At the same time, taking appropriate amounts of Ginkgolic acid C13:0 reference substance, Ginkgolic acid C15:1 reference substance, and Ginkgolic acid C17:1 reference substance, respectively, and precisely weighing the reference substances. The reference substances are added with methanol to prepare a series of mixed solutions respectively containing 0ng/ml, 10 ng/ml, 20 ng/ml, 50 ng/ml, 100 ng/ml and 200 ng/ml of each reference substance, so as to obtain the reference solutions.

Precisely pipetting 1 μl from the test product solutions D1, D2, D3 and the reference solutions, respectively, then determining by high performance liquid chromatography-mass spectrometry (HPLC-MS) in General Rules 0512 and 0431 in Chinese Pharmacopoeia (2015 Edition) Volume IV. The conditions of the HPLC-MS are: octadecylsilane chemically bonded silica gel serves as a filler; methanol-1% glacial acetic acid solution (90:10) serves as the mobile phase, eluting isocratically, fully cleaning with methanol-1% glacial acetic acid solution (99:1) that is at least 10 times the volume of the column after all the components to be determined have reached the peak; triple quadrupole mass spectrometer is used for multiple reaction monitoring (MRM) under electrospray ionization (ESI) negative ion mode. The monitoring ion pairs are shown in Table 3 below. If a chromatographic peak with the same retention time as that of the reference substance is detected in the test product solution, and the selected ion abundance ratio and the ion abundance ratio of the corresponding concentration of the reference solution meet the requirements of Table 4 below, the component can be determined to be present.

TABLE 3

| Name | Parent ion | Quantitative ion pair | Qualitative ion pair |
| --- | --- | --- | --- |
| Ginkgolic acid C13:0 | 319.2 | 319.2→275.2 | 319.2→106.1 |
| Ginkgolic acid C15:1 | 345.2 | 345.2→301.2 | 345.2→119.0 |
| Ginkgolic acid C17:1 | 373.3 | 373.3→329.3 | 373.3→106.0 |

TABLE 4

| Relative ion abundance/% | >50 | 20~50 | 10~20 | <10 |
| --- | --- | --- | --- | --- |
| Allowed relative deviation/% | ±20 | ±25 | ±30 | ±50 |

The determination shows that the contents of total Ginkgolic acids in the *Ginkgo biloba* ketone ester Sample 1# and *Ginkgo biloba* ketone ester Control Sample 1* are 0.8 mg/kg and 4.3 mg/kg, respectively, which are both ≤5 mg/kg. The content of total Ginkgolic acids in *Ginkgo biloba* ketone ester Control Sample 2* is 11.3 mg/kg, which is not only more than 5 mg/kg, but even more than 10 mg/kg. Ginkgolic acids have a sensitizing effect and long-term administration of Ginkgo preparation would cause accumulation of Ginkgolic acids and do harm to the human body. Therefore, the content of Ginkgolic acids in the *Ginkgo biloba* ketone ester must be controlled and kept low. The content of total Ginkgolic acids in the *Ginkgo biloba* ketone ester Control Sample 2* exceeds the limit, which will cause harm to the human body. The contents of total Ginkgolic acids in *Ginkgo biloba* ketone ester Sample 1# and *Ginkgo biloba* ketone ester Control Sample 1* are both within the limit. However, due to the operations such as washing in the preparation method, *Ginkgo biloba* ketone ester Sample 1# has a lower total Ginkgolic acid content, which can reach 1 mg/kg or less, therefore is less likely to cause sensitization.

Embodiment 9

Respectively taking 75 mg from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing, precisely adding 50 ml mixed solution of methanol-25% hydrochloric acid solution (4:1), weighing, placing in 85-90° C. water bath and heating at reflux for 30 minutes, taking out, cooling rapidly to room temperature, weighing again, using the above mixed solution to make up for the weight loss, and shaking well. Filtering, and taking the subsequent filtrate to obtain test product solutions E1, E2 and E3.

At the same time, taking appropriate amounts of a quercetin reference substance, kaempferide reference substance and isorhamnetin reference substance, precisely weighing the reference substances. The reference substances are added with methanol to prepare mixed solutions respectively containing 84 μg, 120 μg, 24 μg of each reference substance per 1 ml, to obtain the reference solution.

Precisely pipetting 10 μl from the test product solutions and the reference solution, respectively, which are then determined by high performance liquid chromatography (HPLC) in General Rules 0512 in Chinese Pharmacopoeia (2015 Edition) Volume IV. The conditions of the high performance liquid chromatography are: octadecylsilane chemically bonded silica gel serves as a filler; methanol-0.4% phosphoric acid solution (49:51) serves as the mobile phase; isocratic elution; the detection wavelength is 368 nm. The number of theoretical plates calculated by the quercetin peak is no less than 4000. The resolution between the kaempferide peak and isorhamnetin peak should be greater than 1.5.

The content of total flavonol glycosides in the *Ginkgo biloba* ketone ester is calculated according to formula (1): content of total flavonol glycosides=(quercetin content+kaempferide content+isorhamnetin content)×2.51.

The determination shows that the contents of total flavonol glycosides in *Ginkgo biloba* ketone ester Sample 1# and *Ginkgo biloba* ketone ester Control Sample 1* are 33.8% and 26.7% (calculated as dry products), respectively, which are within a specified data range of 24.0-35.0%. The content of total flavonol glycosides in *Ginkgo biloba* ketone ester Control Sample 2* is 20.3% (calculated as dry products), which is lower than the specified data range of 24.0-35.0%. Total flavonol glycosides are active substances that contain free flavonoids. A certain amount of total flavonol glycosides in *Ginkgo biloba* ketone ester endows *Ginkgo biloba* ketone ester with a good therapeutic effect. Therefore, the *Ginkgo biloba* ketone ester Control Sample 2* has a poor treatment effect. *Ginkgo biloba* ketone ester Sample 1# and *Ginkgo biloba* ketone ester Control Sample 1* both have good therapeutic effects. However, the content of total flavonol glycosides in *Ginkgo biloba* ketone ester Sample 1# is higher, which is within a specified data range of 30.0-35.0%. Compared with *Ginkgo biloba* ketone ester Control Sample 1*, the *Ginkgo biloba* ketone ester Sample 1# has a better therapeutic effect.

Precisely pipetting 10 μl from the test product solutions E1, E2, E3 and the reference solution, respectively, then determining by the above-mentioned high performance liquid chromatography (HPLC). The determination shows that in *Ginkgo biloba* ketone ester Sample 1# and *Ginkgo biloba* ketone ester Control Sample 1*, the chromatographic peak area ratios of quercetin to kaempferide are 0.91 and 1.02 respectively, which are within the specified data range of 0.8-1.2; the chromatographic peak area ratios of isorhamnetin to quercetin are 0.21 and 0.22 respectively, which are more than 0.15. In *Ginkgo biloba* ketone ester Control Sample 2*, the chromatographic peak area ratio of quercetin to kaempferide is 0.61, lower than the specified data range of 0.8-1.2; the chromatographic peak area ratio of isorhamnetin to quercetin is 0.13, lower than 0.15. It can be seen from the above proportional relationship that there is no adulterated foreign substances in *Ginkgo biloba* ketone ester Sample 1# and *Ginkgo biloba* ketone ester Control Sample 1*, indicating the product process is normal, and the product quality is good. The quality of *Ginkgo biloba* ketone ester Control Sample 2* is poor due to the addition of quercetin and adulterated foreign substances.

Embodiment 10

Respectively taking 50 mg from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing, adding 10 ml of 75% methanol, treating with ultrasonic (power: 300 W, frequency: 50 KHz) for 10 minutes, centrifuging for 5 minutes (4000 rpm), taking the supernatant to obtain the test product solutions F1, F2 and F3.

At the same time, taking appropriate amounts of a rutin reference substance, quercetin reference substance, kaempferide reference substance and isorhamnetin reference substance, precisely weighing the reference substances. The reference substances are added with 75% methanol to prepare a solution containing 30 μg of each reference substance per 1 ml, and the reference solution is obtained.

Precisely pipetting 10 μl from the test product solutions and the reference solution, respectively, which are then determined by high performance liquid chromatography (HPLC) in General Rules 0512 in Chinese Pharmacopoeia (2015 Edition) Volume IV. The conditions of the high-performance liquid chromatography are: octadecylsilane chemically bonded silica gel serves as a filler (length of the column: 15 cm; inner diameter: 4.6 mm; particle size: 5 μm); acetonitrile serves as mobile phase A, and 0.1% formic acid solution serves as mobile phase B. Gradient elution is performed according to the specification in Table 5 below; the detection wavelength is 360 nm; the column temperature is 30° C.; the flow rate is 1.0 ml/min. The number of theoretical plates calculated by the rutin peak is no less than 10000.

TABLE 5

| Time (minutes) | Mobile phase A (%) | Mobile phase B (%) |
| --- | --- | --- |
| 0-40 | 15-30 | 85-70 |
| 40-45 | 30-40 | 70-60 |
| 45-50 | 40 | 60 |
| 50-60 | 40-60 | 60-40 |
| 60-70 | 60 | 40 |

The similarity between the fingerprint spectra of test products and *Ginkgo biloba* ketone ester is calculated and compared according to "Similarity Evaluation System for Chromatographic Fingerprint of Traditional Chinese Medicine" (version 2.0). The fingerprint spectrum of the *Ginkgo biloba* ketone ester includes four common fingerprint peaks as shown in FIG. 1: peak 1 is the fingerprint peak of rutin, peak 6 is the fingerprint peak of quercetin, peak 7 is the fingerprint peak of kaempferide, and peak 8 is the fingerprint peak of isorhamnetin. The determination shows that the similarity between the fingerprint spectra of *Ginkgo biloba* ketone ester Sample 1# and *Ginkgo biloba* ketone ester Control Sample 1* and the chromatogram of the test product are 0.98 and 0.92, respectively, which are both greater than or equal to 0.90. The similarity between the fingerprint spectrum of the *Ginkgo biloba* ketone ester Control Sample 2* and the chromatogram of the test product is 0.3, which is lower than 0.90. It can be seen from the above similarities that there is no adulterated foreign substances in *Ginkgo biloba* ketone ester Sample 1# and *Ginkgo biloba* ketone ester Control Sample 1*, indicating the product quality is good. The quality of *Ginkgo biloba* ketone ester Control Sample 2* is poor due to the addition of adulterated foreign substances.

Embodiment 11

The water content of *Ginkgo biloba* ketone ester in *Ginkgo biloba* ketone ester Sample 1# (prepared in Embodiment 1), the *Ginkgo biloba* ketone ester Control Sample 1* and 2* (prepared in Control Examples 1 and 2, respectively) are calculated according to the second method of General Rules 0832 in Chinese Pharmacopoeia (2015 Edition) Volume IV.

High water content would cause agglomeration and affect the quality of the products. Therefore, the content of water in the *Ginkgo biloba* ketone ester must be controlled and kept low. The determination shows that the contents of water in the *Ginkgo biloba* ketone ester Sample 1#, *Ginkgo biloba* ketone ester Control Sample 1* and *Ginkgo biloba* ketone ester Control Sample 2* are all less than or equal to 5.0%.

Embodiment 12

The ignition residue content of *Ginkgo biloba* ketone ester in *Ginkgo biloba* ketone ester Sample 1# (prepared in Embodiment 1), the *Ginkgo biloba* ketone ester Control Sample 1* and 2* (prepared in Control Examples 1 and 2, respectively) are calculated according to Appendix IX J of the Chinese Pharmacopoeia (2010 edition) Volume I.

A high content of ignition residue indicates that the impurity content is high, which will affect the product quality. Therefore, the content of ignition residue in the *Ginkgo biloba* ketone ester must be controlled and kept low. The determination shows that the contents of ignition residue in the *Ginkgo biloba* ketone ester Sample 1#, *Ginkgo biloba* ketone ester Control Sample 1* and *Ginkgo biloba* ketone ester Control Sample 2* are 0.12%, 0.44% and 0.45%, respectively, which are all less than 0.5%. However, due to the operations such as washing in the preparation method, *Ginkgo biloba* ketone ester Sample 1# has a lower ignition residue content, which can reach≤0.2%, therefore has better product quality.

Embodiment 13

Respectively taking 0.8 g from the *Ginkgo biloba* ketone ester Sample 1# (prepared in Embodiment 1), the *Ginkgo biloba* ketone ester Control Sample 1* and 2* (prepared in Control Examples 1 and 2, respectively), precisely weighing the samples, placing the samples in 20 ml headspace bottles, precisely adding 5 ml of dimethylformamide, sealing the bottle opening, shaking to dissolve, shaking well, and obtaining test product solutions G1, G2 and G3.

At the same time, taking an appropriate amount of cyclohexane, precisely weighing the cyclohexane, adding with dimethylformamide to prepare a solution containing 1.8 μg per 1 ml as the reference solution. Precisely measuring 0.5 ml of the reference solution into a 20 ml headspace bottle, sealing the bottle opening, shaking well, and the reference solution is obtained.

Precisely sucking 1 ml of gasified gas from the test solution G1, G2, G3 and the reference solution, respectively. According to the second method of General Rules 0861 in Chinese Pharmacopoeia (2015 Edition) Volume IV, the gasified gas is injected into a gas chromatograph, the chromatogram is recorded, and the peak area is calculated according to the external standard method.

Cyclohexane is a chemical solvent. Too much residual cyclohexane would cause harm to the human body. Therefore, the content of cyclohexane in the *Ginkgo biloba* ketone ester must be controlled and kept low. The determination shows that the contents of cyclohexane residue in the *Ginkgo biloba* ketone ester Sample 1#, *Ginkgo biloba* ketone ester Control Sample 1* and *Ginkgo biloba* ketone ester Control Sample 2* are 0.0003%, 0.0018% and 0.0019%, respectively, which are all less than or equal to 0.002%. However, due to the operations such as washing in the preparation method, *Ginkgo biloba* ketone ester Sample 1# has a lower cyclohexane residue content, which can reach≤0.001%, therefore has better product quality and is less likely to cause harm to human body.

Embodiment 14

The contents of lead, cadmium, arsenic, mercury, and copper in *Ginkgo biloba* ketone ester Sample 1# (prepared in Embodiment 1), the *Ginkgo biloba* ketone ester Control Sample 1* and 2* (prepared in Control Examples 1 and 2, respectively) are determined according to the lead, cadmium, arsenic, mercury, and copper determination method described in General Rules 2321 in Chinese Pharmacopoeia (2015 Edition).

The determination shows that in the *Ginkgo biloba* ketone ester Sample 1#, *Ginkgo biloba* ketone ester Control Sample 1* and *Ginkgo biloba* ketone ester Control Sample 2*, the contents of lead are 0.5 mg/kg, 2.2 mg/kg and 2.3 mg/kg, respectively, which are all ≤3.0 mg/kg; the contents of cadmium are 0.08 mg/kg, 0.15 mg/kg and 0.16 mg/kg, respectively, which are all ≤0.2 mg/kg; the contents of arsenic are 0.6 mg/kg, 1.7 mg/kg and 1.8 mg/kg, respectively, which are all ≤2.0 mg/kg; the contents of mercury are 0.02 mg/kg, 0.08 mg/kg and 0.09 mg/kg, respectively, which are all ≤0.1 mg/kg; the contents of copper are 6 mg/kg, 16 mg/kg and 17 mg/kg, respectively, which are all ≤20 mg/kg. Heavy metals are toxic. Therefore, for *Ginkgo biloba* ketone ester, the lower the content of heavy metals, the better the product quality. The contents of heavy metal elements in the *Ginkgo biloba* ketone ester Sample 1#, *Ginkgo biloba* ketone ester Control Sample 1* and *Ginkgo biloba* ketone ester Control Sample 2* are all within the limit. Therefore, the product quality meets the requirements. However, *Ginkgo biloba* ketone ester Sample 1# has the best product quality due to its lowest content of heavy metal elements.

Embodiment 15

The contents of pesticide residues in *Ginkgo biloba* ketone ester Sample 1# (prepared in Embodiment 1), the *Ginkgo biloba* ketone ester Control Sample 1* and 2* (prepared in Control Examples 1 and 2, respectively) are determined according to the pesticide residue determination method described in General Rules 2341 in Chinese Pharmacopoeia (2015 Edition) Volume IV.

The determination shows that in the *Ginkgo biloba* ketone ester Sample 1#, *Ginkgo biloba* ketone ester Control Sample 1* and *Ginkgo biloba* ketone ester Control Sample 2*, the contents of total BHC are 0.01 mg/kg, 0.08 mg/kg and 0.16 mg/kg, respectively, which are all ≤0.2 mg/kg; the contents of total DDT are 0.02 mg/kg, 0.09 mg/kg and 0.15 mg/kg, respectively, which are all ≤0.2 mg/kg; the contents of pentachloronitrobenzene are 0.008 mg/kg, 0.03 mg/kg and 0.08 mg/kg, respectively, which are all ≤0.1 mg/kg; the contents of dichlorvos are 0.08 mg/kg, 0.13 mg/kg and 0.34 mg/kg, respectively, which are all ≤0.5 mg/kg; the contents of methamidophos are 0.011 mg/kg, 0.023 mg/kg and 0.041 mg/kg, respectively, which are all ≤0.05 mg/kg; the contents of acephate are 0.01 mg/kg, 0.032 mg/kg and 0.086 mg/kg, respectively, which are all ≤0.1 mg/kg; the contents of ethion are 0.07 mg/kg, 0.16 mg/kg and 0.32 mg/kg, respectively, which are all ≤0.5 mg/kg; the contents of omethoate are 0.009 mg/kg, 0.014 mg/kg and 0.038 mg/kg, respectively, which are all ≤0.05 mg/kg; the contents of diazinon are 0.04 mg/kg, 0.17 mg/kg and 0.41 mg/kg, respectively, which are all ≤0.5 mg/kg; the contents of methidathion are 0.007 mg/kg, 0.021 mg/kg and 0.039 mg/kg, respectively, which are all ≤0.05 mg/kg; the contents of monocrotophos are 0.011 mg/kg, 0.041 mg/kg and 0.087 mg/kg, respectively, which are all ≤0.1 mg/kg; the contents of dimethoate are 0.018 mg/kg, 0.053 mg/kg and 0.091 mg/kg, respectively, which are all ≤0.1 mg/kg; the contents of parathion-methy are 0.008 mg/kg, 0.033 mg/kg and 0.071 mg/kg, respectively, which are all ≤0.1 mg/kg; the contents of cypermethrin are 0.06 mg/kg, 0.43 mg/kg and 0.61 mg/kg, respectively, which are all ≤1 mg/kg; the contents of fenvalerate are 0.11 mg/kg, 0.23 mg/kg and 0.41 mg/kg, respectively, which are all ≤0.5 mg/kg; the contents of deltamethrin are 0.09 mg/kg, 0.24 mg/kg and 0.38 mg/kg, respectively, which are all ≤0.5 mg/kg. Pesticide residues are toxic. Therefore, for *Ginkgo biloba* ketone ester, the lower the content of pesticide residues, the better the product quality. The contents of pesticide residues in the *Ginkgo biloba* ketone ester Sample 1#, *Ginkgo biloba* ketone ester Control Sample 1* and *Ginkgo biloba* ketone ester Control Sample 2* are all within the limit. Therefore, the product quality meets the requirements. However, *Ginkgo biloba* ketone ester Sample 1# has the best product quality due to its lowest content of pesticide residues.

Embodiment 16

The contents of aflatoxins in *Ginkgo biloba* ketone ester Sample 1# (prepared in Embodiment 1), the *Ginkgo biloba* ketone ester Control Sample 1* and 2* (prepared in Control Examples 1 and 2, respectively) are determined according to the aflatoxin determination method described in General Rules 2351 in Chinese Pharmacopoeia (2015 Edition) Volume IV. The aflatoxins include aflatoxin G2, aflatoxin G1, aflatoxin B2, and aflatoxin B1.

The determination shows that the total contents of aflatoxins in every 1000 g of the *Ginkgo biloba* ketone ester Sample 1#, *Ginkgo biloba* ketone ester Control Sample 1* and *Ginkgo biloba* ketone ester Control Sample 2* are 0.8 μg, 2.1 μg and 3.8 μg, respectively, which are all less than or equal to 4 μg. At the same time, the contents of aflatoxin B1 in every 1000 g of the *Ginkgo biloba* ketone ester Sample 1#, *Ginkgo biloba* ketone ester Control Sample 1* and *Ginkgo biloba* ketone ester Control Sample 2* are 0.3 μg, 1.0 μg and 1.6 μg, respectively, which are all less than or equal to 2 μg. Aflatoxins are liable to cause cancer. Therefore, for *Ginkgo biloba* ketone ester, the lower the content of aflatoxins, the better the product quality. The contents of aflatoxins in the *Ginkgo biloba* ketone ester Sample 1#, *Ginkgo biloba* ketone ester Control Sample 1* and *Ginkgo biloba* ketone ester Control Sample 2* are all within the limit. Therefore, the product quality meets the requirements. However, *Ginkgo biloba* ketone ester Sample 1# has the best product quality due to its lowest content of aflatoxins.

Embodiment 17

*Ginkgo biloba* nursery leaves that serve as the medicinal raw materials in Embodiment 1 are selected and dried at 140-160° C. for 6-15 minutes, to serve as the raw material Sample 1; at the same time, conventional *Ginkgo biloba* leaves that serve as the medicinal raw materials in Control Example 1 are selected to serve as the raw material Sample 2.

The contents of total flavonol glycosides and the chromatographic peak area ratios of flavonoid aglycones in raw material Sample 1 and raw material Sample 2 are determined according to the method described in Embodiment 9. The contents of terpene lactone in raw material Sample 1 and raw material Sample 2 are determined by the method described in Embodiment 4. The contents of total ash and acid-insoluble ash in raw material Sample 1 and raw material Sample 2 are determined according to the ash determination method described in General Rules 2302 in Chinese Pharmacopoeia (2015 Edition) Volume IV. The contents of extractum in raw material Sample 1 and raw material Sample 2 are determined according to the extractum determination method described in General Rules 2201 in Chinese Pharmacopoeia (2015 Edition) Volume IV. The contents of impurity in raw material Sample 1 and raw material Sample 2 are determined according to the impurity determination method described in General Rules 2301 in Chinese Pharmacopoeia (2015 Edition) Volume IV. The contents of water in raw material Sample 1 and raw material Sample 2 are determined according to the water determination method described in General Rules 0832 in Chinese Pharmacopoeia (2015 Edition) Volume IV. The contents of sulfur dioxide residue in raw material Sample 1 and raw material Sample 2 are determined according to the sulfur dioxide residue determination method described in General Rules 2331 in Chinese Pharmacopoeia (2015 Edition) Volume IV.

The determination shows that the contents of total flavonol glycosides in raw material Sample 1 and raw material Sample 2 are 1.34% and 0.54%, respectively. The content of total flavonol glycosides in raw material Sample 2, though meets the requirement of the Pharmacopoeia that the content of total flavonol glycosides is greater than or equal to 0.40%, does not meet the requirement specified in the present disclosure that the content of total flavonol glycosides is greater than or equal to 0.85%. The content of total flavonol glycosides in raw material Sample 1 is not only greater than or equal to 0.40%, but also greater than or equal to 0.85%. The raw material Sample 1 has a higher content of total flavonol glycosides, therefore has better raw material quality.

The determination shows that the contents of terpene lactones in raw material Sample 1 and raw material Sample 2 are 0.62% and 0.33%, respectively. The content of terpene lactones in raw material Sample 2, though meets the requirement of the Pharmacopoeia that the content of terpene lactones is greater than or equal to 0.25%, does not meet the requirement specified in the present disclosure that the content of terpene lactones is greater than or equal to 0.40%. The content of terpene lactones in raw material Sample 1 is not only greater than or equal to 0.25%, but also greater than or equal to 0.40%. The raw material Sample 1 has a higher content of terpene lactones, therefore has better raw material quality.

The determination shows that the chromatographic peak area ratios of quercetin to kaempferide in raw material Sample 1 and raw material Sample 2 are 0.87 and 0.55, respectively. Raw material Sample 1 meets the data range of 0.65-1.2 specified in the present disclosure, while raw material Sample 2 does not meet the data range of 0.65-1.2 specified in the present disclosure. The chromatographic peak area ratios of isorhamnetin to quercetin in raw material Sample 1 and raw material Sample 2 are 0.21 and 0.14, respectively. Raw material Sample 1 meets the requirement of >0.15 specified in the present disclosure, while raw material Sample 2 does not meet the requirement of >0.15 specified in the present disclosure. It can be seen from the above proportional relationship that as raw material, the quality of raw material Sample 1 is better than that of raw material Sample 2.

The determination shows that the contents of sulfur dioxide residues in raw material Sample 1 and raw material Sample 2 are 11 mg/kg and 88 mg/kg, respectively, which are both ≤150 mg/kg. The contents of sulfur dioxide residues in raw material Sample 1 and raw material Sample 2 are all within the limit. Therefore, the raw material qualities of raw material Sample 1 and raw material Sample 2 meet the requirements. However, raw material Sample 1 has better raw material quality due to its lower content of sulfur dioxide residue.

At the same time, the determination shows that the total ash content in raw material Sample 1 and raw material Sample 2 are 3.8% and 6.9%, respectively, which are both ≤10.0%. The acid-insoluble ash content in raw material Sample 1 and raw material Sample 2 are 0.68% and 1.54%, respectively, which are both ≤2.0%. The extractum content in raw material Sample 1 and raw material Sample 2 are 44.1% and 28.2%, respectively, which are both ≥25.0%. The impurity content in raw material Sample 1 and raw material Sample 2 are 0.57% and 1.33%, respectively, which are both ≤2.0%. The water content in raw material Sample 1 and raw material Sample 2 are 5.3% and 10.1%, respectively, which are both ≤12.0%. It can be seen that the above-mentioned contents in raw material Sample 1 and raw material Sample 2 are all within the specified limit range, and the quality of the raw materials meets the requirements. However, the relevant content indicators of raw material Sample 1 are better than that of raw material Sample 2. Therefore, the quality of raw material Sample 1 is better. Using the raw material Sample 1, it's possible to prepare *Ginkgo biloba* ketone ester bulk drug samples with better quality.

As mentioned above, the present disclosure provides a *Ginkgo biloba* ketone ester and a preparation method thereof. Through optimized preparation operations and conditions, high-quality *Ginkgo biloba* ketone ester can be obtained. Compared with the *Ginkgo biloba* ketone ester prepared by traditional methods, the *Ginkgo biloba* ketone ester of the present disclosure has stable quality, low unqualified rate, and good consistency of different batches of bulk drugs. Therefore, the present disclosure effectively overcomes various shortcomings in the existing technology and has high industrial utilization value.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

The invention claimed is:

1. A method for preparing a *Ginkgo biloba* ketone ester bulk drug, comprising the following operations:
    A) adding ethanol aqueous solution to crushed *Ginkgo biloba* leaves, heating at reflux for extraction, and then obtaining a filtrate by filtration;
    B) concentrating the filtrate and performing water-sedimentation, centrifuging a supernatant to obtain a centrifugal liquid;
    C) loading the centrifugal liquid onto a macroporous resin column, then washing with water and eluting with solvent to obtain a first eluent; the first eluent includes a low-concentration-solvent first eluent and a high-concentration-solvent first eluent;
    D) loading the low-concentration-solvent first eluent onto a polyamide column, then washing with water and eluting with ethanol to obtain a second eluent;

E) combining and concentrating the second eluent with the high-concentration-solvent first eluent, and then extracting, drying, crushing, sieving, and mixing to obtain a *Ginkgo biloba* ketone ester drug;

wherein the obtained *Ginkgo biloba* ketone ester bulk drug meets the following conditions:
1) the content of rutin is less than or equal to 4.0%;
2) the content of quercetin is less than or equal to 0.4%;
3) the content of bilobalide is 2.6-4.8%;
4) the content of Ginkgolide J is 0.1-0.5%;
5) the content of residual ethanol is less than or equal to 0.5%;
6) the content of biflavonoids is less than or equal to 0.02%, wherein the biflavonoids include amentoflavone, bilobetin, and ginkgetin;
7) the content of genistin is 0, and the content of ginkgolide M is 0.

2. The method for preparing the *Ginkgo biloba* ketone ester bulk drug according to claim 1, wherein in operation A), the obtaining of the filtrate includes the following:
   C1) adding 60% ethanol aqueous solution to crushed *Ginkgo biloba* leaves, heating at reflux for extraction, and then obtaining a first filtrate by filtration;
   C2) adding water to a residual medicine residue after the filtration in operation C1), heating at reflux for extraction, and then obtaining a second filtrate by filtration;
   C3) combining and concentrating into a thick paste the second filtrate in operation C2) and the first filtrate in operation C1), dissolving, standing to cool, and filtering to obtain a desired filtrate.

3. The method for preparing the *Ginkgo biloba* ketone ester bulk drug according to claim 1, wherein in operation C), the washing with water is forward-washing with purified water for 1-2 hours first, and then backwashing for 0.5-1.5 hours; in operation D), the washing with water is forward-washing by using purified water 0.5-2 times the volume of the polyamide column.

4. The method for preparing the *Ginkgo biloba* ketone ester bulk drug according to claim 1, wherein operation E) includes one or more of the following:
   F1) the sieving is by passing through a 80-100 mesh sieve;
   F2) conditions for the mixing are: a mixing equipment is a total mixer; a mixing speed is 10-12 rpm; a mixing time is 1.5-2.5 hours.

* * * * *